United States Patent [19]
Eisenfeld

[11] Patent Number: 5,555,891
[45] Date of Patent: Sep. 17, 1996

[54] VIBROTACTILE STIMULATOR SYSTEM FOR DETECTING AND INTERRUPTING APNEA IN INFANTS

[75] Inventor: Leonard I. Eisenfeld, West Hartford, Conn.

[73] Assignee: Hartford Hospital, Hartford, Conn.

[21] Appl. No.: 424,590

[22] Filed: Apr. 17, 1995

Related U.S. Application Data

[63] Continuation of Ser. No. 247,049, May 20, 1994, abandoned.

[51] Int. Cl.$^6$ ...................................................... A61B 5/00
[52] U.S. Cl. ........................................... 128/721; 128/782
[58] Field of Search ................................... 128/721, 722, 128/774, 782, 723; 340/573

[56] References Cited

U.S. PATENT DOCUMENTS

| | | | |
|---|---|---|---|
| 4,630,614 | 12/1986 | Atlas | 128/721 |
| 4,648,407 | 3/1987 | Sackner | 128/721 |
| 4,657,026 | 4/1987 | Tagg | 123/721 |
| 4,671,297 | 6/1987 | Schulze, Jr. | 128/721 X |
| 4,686,999 | 8/1987 | Snyder et al. | 128/721 X |
| 4,694,839 | 9/1987 | Timme | 128/721 |
| 4,851,816 | 7/1989 | Macias et al. | 340/573 |
| 5,105,354 | 4/1992 | Nishimura | 364/413.03 |
| 5,107,855 | 4/1992 | Harrington | 128/721 |
| 5,178,156 | 1/1993 | Takishima et al. | 128/724 |
| 5,191,893 | 3/1993 | Reiten | 128/721 |
| 5,241,300 | 8/1993 | Buschmann | 128/721 X |

OTHER PUBLICATIONS

Finer et al, "Obstructive, mixed, and central apnea in the neonate: Physiologic correlates", *The Journal of Pediatrics*, Dec. 1992, pp. 943–949.
Kaczmarek et al, "Electrotactile and Vibrotactile Displays for Sensory Substitution Systems", IEEE *Transactions on Biomedical Engineering*, vol. 38, No. 1, Jan. 1991.
Garcia et al., "Preterm Infants' Responses to Taste/Smell and Tactile Stimulation During an Apneic Episode", *Journal of Pediatric Nursing*, vol. 8, No. 4, Aug. 1993, pp. 245–252.
Miller et al, "Apnea of Prematurity", *Clinics in Perinatology*, vol. 19, No. 4, Dec. 1992, pp. 789–808.
Korner et al, "Effects of Waterbed Flotation on Premature Infants: A Pilot Study", *Pediatrics*, vol. 56, No. 3, Sep. 1975, pp. 361–367.
Serafini et al, "Antepartum fetal heart rate response to sound stimulation: The acoustic stimulation test", *Am J. Obstet. Gynecol.*, Jan. 1, 1984, pp. 41–45.
Schlaefke et al, "Transcutaneous Monitoring as Trigger for Therapy of Hypoxemia During Sleep", *Advances in Experimental Medicine & Biology*, 220:95–100, 1987.
Steinbach et al, "Apnea Triggered Stimulation to Reduce Apnea of Prematurity", *Neonatal Intensive Care*, Nov./Dec. 1992, pp. 17–18.

*Primary Examiner*—Sam Rimell
*Attorney, Agent, or Firm*—Chilton, Alix & Van Kirk

[57] ABSTRACT

A vibrotactile stimulator system for detecting and interrupting apnea in premature neonates comprises a multi-sensing monitor for detecting the respiration and other physiological characteristics of the neonate, a vibrotactile sensory stimulator in contact with an extremity of the neonate and a computer interface functionally positioned between the monitor and the vibrotactile stimulator. The interface provides a comparison of the monitored data to preprogrammed individualized standards to determine variations from the standard and provides an intervention output signal to the vibrator. The stimulator includes a cutaneous vibrator engaging a peripheral sensory area of the neonate and being operable at a frequency up to about 400 Hz, but optimally about 260 Hz, to stimulate the neonate and interrupt an apneic episode. The system can include time-delayed, backup, audible and/or visual alarms as well as a graphic display with a pre-apneic printout and cribside or remote manual actuation capability.

28 Claims, 3 Drawing Sheets

VIBROTACTILE STIMULATOR SYSTEM FOR DETECTING AND INTERRUPTING APNEA IN INFANTS

This is a continuation of application Ser. No. 08/247,049 filed on May 20, 1994, now abandoned.

BACKGROUND

1. Field of the Invention

The present invention relates generally to a system for interrupting apnea in infants. More particularly, it is concerned with a new and improved vibratory stimulator system for detecting and interrupting apnea in infants, especially premature neonates.

2. Description of the Prior Art

Apnea is among the major respiratory control disorders in premature neonates and infants at high risk for the Sudden Infant Death Syndrome. Premature and other infants frequently possess weak, slow or underdeveloped body functions that may result in breathing or respiratory failure. This condition affects about 80 percent of neonates born at less than 30 weeks of gestation and occurs in 84 to 90 percent of infants with birth weights of less than 1,000 grams. Consequently, it can be a significant factor contributing to the mortality of premature infants.

The definition of apnea varies, but is generally considered to be a cessation of respiration for 20 seconds or more. This respiratory failure is particularly deleterious when accompanied by bradycardia, a heart rate reduction to a level of less than 100 beats per minute, and a decrease in blood oxygen saturation. Apnea has been classified into types categorized as either central, obstructive or mixed. The central type of apnea results in a stoppage of activity of the respiratory center evidenced by a disappearance of thoracic and abdominal movements coupled with termination of respiration at the nostrils and mouth. It appears to be the result of an immature nervous system, specifically, the brain stem which regulates respiration, and the failure to expel carbon dioxide, resulting in its accumulation. Obstructive apnea is a respiratory interruption usually occurring in the upper airway despite respiratory efforts by thoracic and/or abdominal movements, thus indicating an obstruction. Mixed apnea is a combination of central and obstructive apnea with either being the initial component.

Current attempts at treating apnea include a pharmacological approach employing the use of specific drugs that increase the respiratory center output, thereby increasing carbon dioxide response and stimulating peripheral chemoreceptors. Other approaches at preventing or treating the apneic spells included the use of oscillating waterbeds or oscillating air mattresses in an attempt to stimulate the infant's body functions. However, the efficacy of such oscillatory treatment has been questioned since the oscillation systems only allow the bed to move the infant at a specific and quite slow rhythmic rate irrespective of the respiratory pattern of the infant. Often the infant becomes conditioned to the rhythmic movement and the effect is negated. A device for responding to obstructive apnea only is described in U.S. Pat. No. 5,178,156. It employs a genioglossus stimulator that acts on the dilator muscles, the throat or upper airway.

Generally, the most effective form of apneic interruption is performed by the infant's nurse who gently shakes or rouses the infant so that breathing resumes. Unfortunately, such tactile stimulation is only successful when the apneic episode is not protracted. Since the personal tactile stimulation by a nurse is most effective, apnea monitors have been developed for detecting the apneic condition and providing a loud audible alarm so that a nurse or other care giver can respond to provide the necessary manual stimulation. If unsuccessful, it may ultimately be necessary to artificially ventilate the infant or provide cardiopulmonary resuscitation. However, current practice in neonatal intensive care facilities emphasizes a reduction in noise levels within the intensive care unit due to the adverse impact of such an environment on the premature infants. Additionally, manual stimulation is inconsistent, often delayed, may include risk of infection due to inadequate handwashing and can result in overstimulation. Accordingly, it is desirable to provide a system that does not rely exclusively upon an audible alarm system and is administered at a more consistent, controlled level.

SUMMARY OF THE INVENTION

Accordingly, it is an object of the present invention to provide a tactile stimulator system that imparts tactile cutaneous vibration to the infant at the onset of an apneic episode as a rapid response in order to modify the respiratory pattern of the infant and terminate the apneic episode. Included in this object is the provision for a vibrotactile stimulator system that incorporates a neonatal monitor and programmed computer interface with the stimulator to provide a rapid detection of and response to an apneic event. The preprogrammed interface can permit adjustable actuation and response levels that differ for each individual infant and can vary both the frequency and intensity of the stimulus. The vibrotactile stimulator system of the type described can be readily attached to a limb or trunk area of the infant to provide a gentle and specific vibration sufficient to cause resumption of breathing by the infant in rapid response to an apneic episode, particularly an episode of the central apnea type.

Yet another object of the present invention is to provide a system of the type described that will effect stimulation of peripheral cutaneous nerves in symptomatic apneic infants, which system is capable of using a range of vibrotactile intensities, frequencies and periods of stimulation. Included in this object is the provision for sensing the heart and respiratory rates of the infant along with other physiological functions such as oxygen saturation and nasal air flow, for analyzing the received information, and for comparing that information to a preprogrammed standard or parameter, such that variations in the physiological data will automatically trigger the operation of mechanical vibration to be imparted to the extremity or trunk of the infant being monitored. The system can include time-delayed, backup, audible and/or visual alarms as well as a graphic display with a pre-apneic printout and a cribside or remote manual actuation capability.

Other objects, features and advantages will be in part obvious and in part pointed out more in detail hereinafter.

These and related results are achieved by providing a vibrotactile stimulator system for detecting and interrupting apnea in infants that comprises a multi-sensing monitor for detecting the respiration characteristics of the infant and providing a comparison of the data to preprogrammed individualized standards to determine variations from these standards. An interface is provided between the monitor and the stimulator that includes an intervention output for signaling the presence of an apneic condition which may be custom-defined by the practicing medical personnel. For example, a single function, such as a pause of respiration of specified duration, may be selected to trigger the stimulator. However, any combination of respiratory pause duration, heart rate deceleration, lack of nasal air flow and/or decrease in oxygen saturation may be programmed to define a treatable event. The system further incorporates a vibrotactile sensory stimulator responsive to the output signal. The stimulator includes a cutaneous vibrator engaging a peripheral sensory area of the infant and being operable at a frequency up to about 400 Hz, but optimally about 260 Hz, to stimulate the infant and interrupt the apneic episode. Another vibrator feature is a sweep mode with pulsating frequencies between 150 to 380 Hz in order to prevent potential infant habituation.

A better understanding of the objects, advantages, features, properties and relationships of the invention will be obtained from the following detailed description and accompanying drawings which set forth an illustrative embodiment and are indicative of the way in which the principles of the invention are employed.

DESCRIPTION OF THE PREFERRED EMBODIMENT

Figure 1:
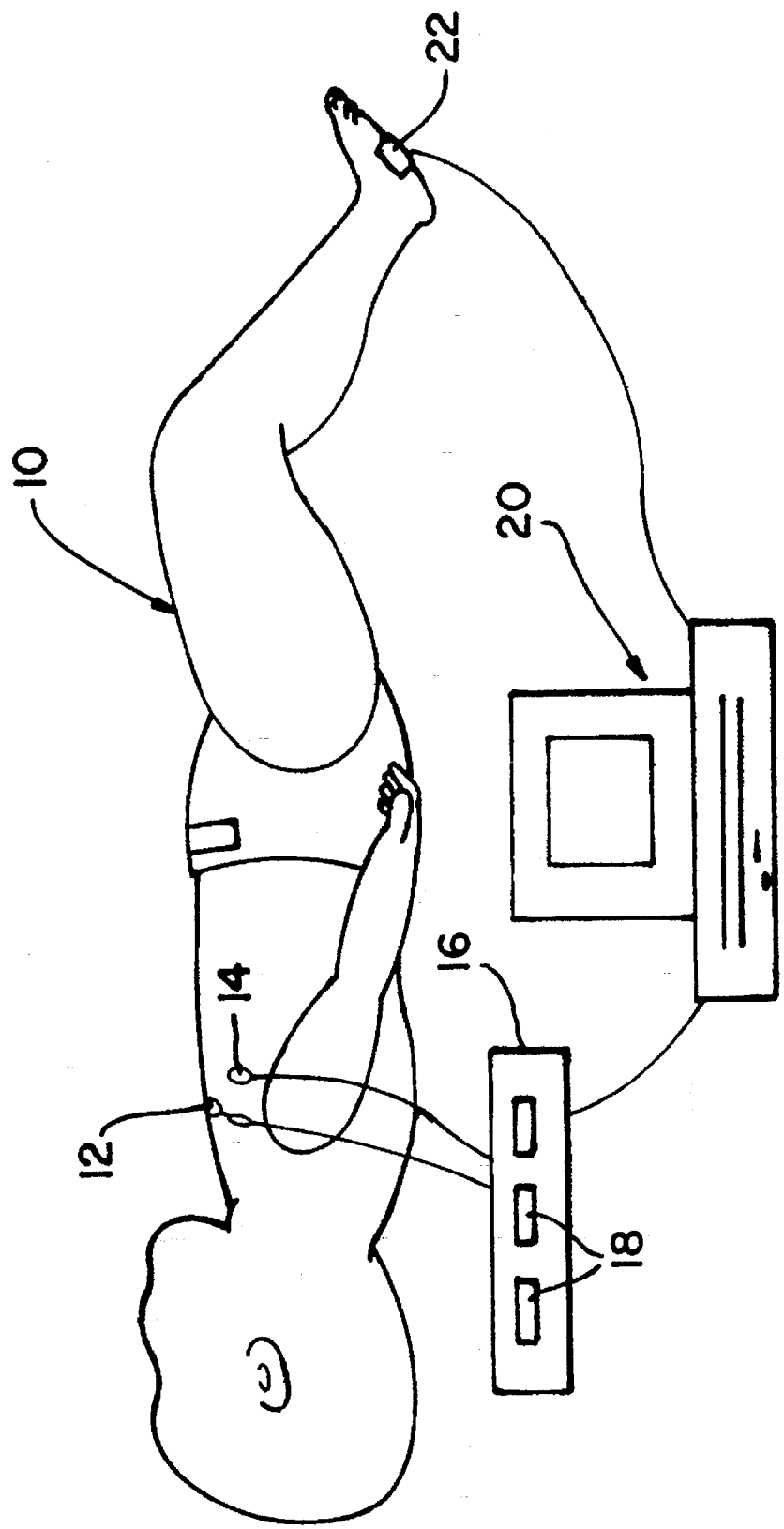
FIG. 1 is a schematic illustration of the vibrotactile stimulator system of the present invention and its application to an infant subject to apnea.

Referring now to the drawings in greater detail, wherein like reference numerals indicate like parts throughout the figures, FIG. 1 shows the system of the present invention in use for a newborn infant at high risk for an apneic episode. The infant, designated 10, is shown being monitored by two or more multi-channel sensors 12, 14 attached to the infant's torso. The sensors are of standard construction and operation and are designed and configured to sense preferably the heart rate and respiratory rate by thoracic impedance of the infant, as well as the oxygen saturation level and other physiological conditions of the infant. Nasal thermistors may be employed to define a treatable event or assist in differentiating between central apnea and obstructive apnea. Other sensors or probes may include an electrocardiogram, electroencephalogram, esophageal pH, or the blood pressure of the infant. As will be appreciated, multiple functions may be monitored using a single sensor pad, or multiple pads or probes may be employed. Optionally, all sensor probes can be wireless. The minimum effective configuration usually would include the heart rate sensor, which detects the pulse of the infant, and the respiratory rate sensor, which detects the expansion and contraction of the infant's chest, are essential sensor channels. However, in some instances it is preferred that the nasal thermistor and/or the oxygen saturation sensor be employed.

The respiratory and cardiac information detected by the sensors is conveyed to an appropriate neonatal monitor 16, and the values for each function are preferably displayed by the monitor at display areas 18. The detected functions typically are reported by the monitor 16 as an analogue output to a central control computer 20 that interfaces with a stimulator 22, the operation of the computer being appropriately controlled by a software program. The computer in turn processes the information from the monitor and controls the operation of the vibrotactile stimulator 22 for interrupting an apneic episode. Accordingly, the system of the present invention consists of three primary components 1) a multi-sensing monitor 16 for measuring certain physiological conditions of the infant, 2) a vibrotactile sensory stimulator 22, preferably in contact with an extremity of the infant, such as the infant's foot or hand, but potentially the thorax, abdomen, back or sides, and 3) a computer interface 20 functionally positioned between the monitor 16 and the vibrotactile stimulator 22 to receive the monitored signals from the infant and control the operation of the stimulator 22.

Figure 2:
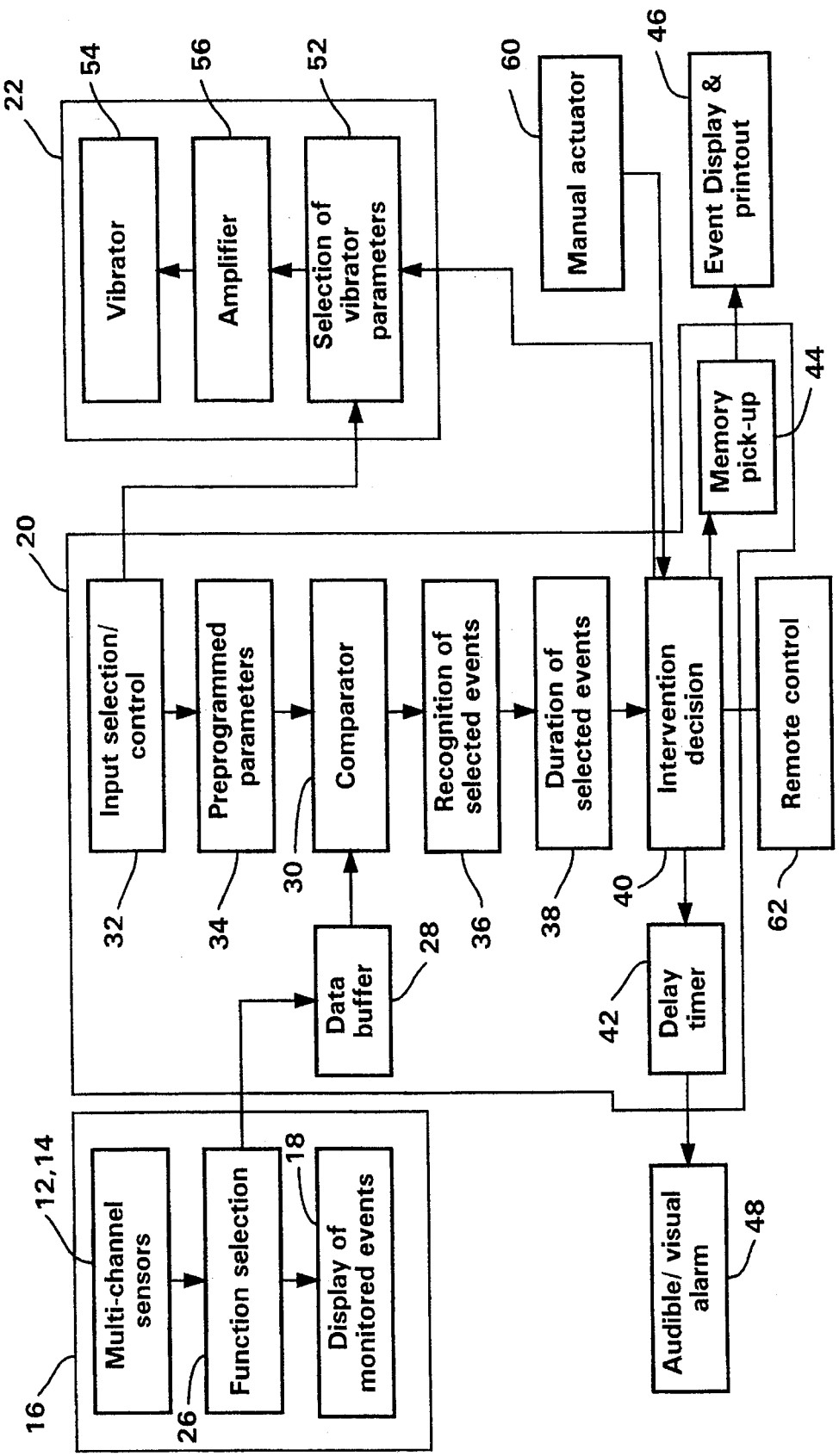
FIG. 2 is a block diagram flow chart showing the operation of the system and the interrelationships between the components thereof.
Figure 3A:
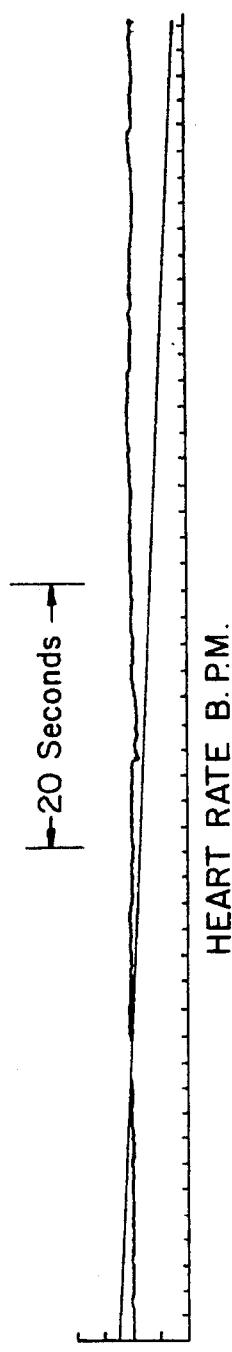
FIG. 3 is a multi-track recording chart of selected physiological functions during an apneic episode including operation of the vibratory interruption thereof.
Figure 3B:
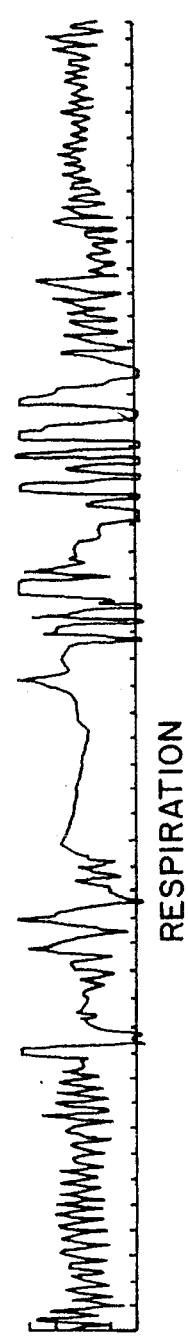
Figure 3C:
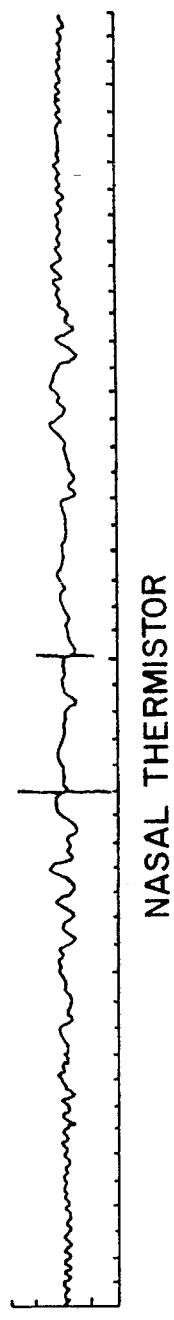
Figure 3D:
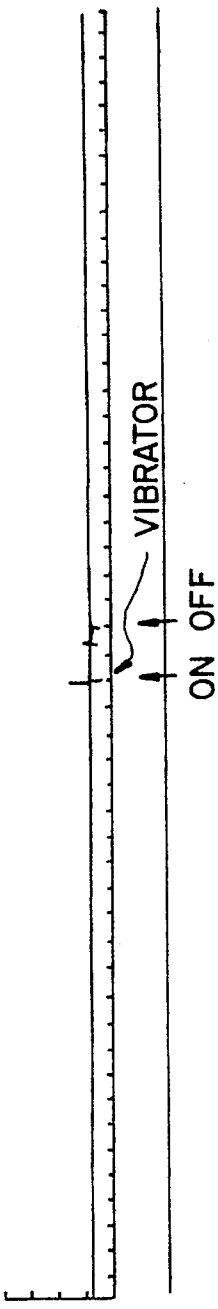

Referring now to FIG. 2, the monitor 16 includes, in addition to the sensors 12, 14, a function selector 26 which permits the operator to select those physiological function to be monitored by the sensors. Data from the sensors are displayed on the monitor display panels 18. As can be appreciated, the operations of the function selector 26 can also be controlled, if desired, by the computer 20, but in its preferred mode is provided at the monitor for operator convenience.

The analogue signals from the monitor are run to a data acquisition board or buffer 28 of the computer for conversion to a digital format before passing to a comparator 30 where the various physiological functions of the infant are compared to preprogrammed parameters for each of the selected functions. In this connection, the computer 20 includes not only an input control or selector 32, such as a keyboard and appropriate software, but also a program that selects automatic default parameters for the sensed physiological functions and vibrator output. The program permits an override of the default values so that the operator may input new manually designated parameters into the unit reflecting the particular needs of individual infants. Thus, the input selection is controlled at the selector 32 which provides either manually chosen specific parameters for the infant or automatic preprogrammed default parameters as indicated at 34.

For example, a heart rate or pulse function may have a preprogrammed alert parameter or standard of 100 beats per minute. The mean resting heart rate for infants before apnea typically is in the range of about 120 to 160 beats per minute. A reduction in the heart rate to less than 100 beats per minute typically occurs in about 80 to 85 percent of those infants that experience central apnea episodes. Accordingly, by providing a preprogrammed parameter of 100 beats per minute, a reduction in the normal level by about as much as 20 percent or more would be permitted before the heart rate would approach the limiting parameter necessary to activate the vibrotactile stimulator. Of course, as mentioned, the parameter may be changed depending on the particular infant involved by simply overriding the preprogrammed parameter or standard and inserting a specific parameter for the individual infant.

The data received from the monitor is compared to the preprogrammed parameters at the comparator 30 so that, if the data falls below the designated parameter, an apnea event will be indicated by the event recognition module 36. The initiation of an apneic event in turn will trigger the start of a timing mechanism to track the duration of the apnea in accordance with preprogrammed control parameters. The event duration 38 withholds transmission of the stimulator activation signal until the recognized event has persisted for the selected length of time. Thus, the event duration parameter may be set at 15 seconds so as to avoid actuation of the stimulator as a result of a false signal of short duration. Upon exceeding the preprogrammed event duration parameter, a signal is sent to actuate an intervention decision module 40 and provide an output signal activating the vibrator unit.

Simultaneous with the actuation of the intervention decision 40, an alarm delay timer 42 is actuated, as is a memory pickup 44 for recording the monitored functions of the infant over a period extending back to at least 30 seconds or more prior to the implementation of the intervention decision. The memory pickup 44 activates the display printout or recording chart 46 so that the entire sensed history from a period prior to onset of the apnea episode, as well as the duration, magnitude and timing of the vibrational intervention is recorded on the display printout 46. Additionally, after the preset period, the delay timer 42 will actuate an audible and/or visual alarm 48 so that the nurse or other caretaker may respond and intervene in the stimulation of the infant, if necessary, so as to interrupt the apneic episode.

The stimulator activation output signal from the intervention decision module 40 passes from the computer to an appropriate selective modulator or function generator 52 of the stimulator unit 22. The modulator in turn controls the pulses conveyed to the vibrator 54 through an appropriate amplifying system 56. As can be appreciated, a wireless connection can be provided between the amplifier and the vibrator. The modulator 52 can be set at a preselected level to provide vibrations of the appropriate intensity, frequency and periodicity. Of course, an indicated in FIG. 2, the modulator 52 also may be controlled by the input control 32 to provide either the preprogrammed vibrotactile stimulation or user selected levels of intensity, frequency or periodicity of the vibration. For example, the vibration may be continuous at a constant level for a designated period of time, or its duration may be interrupted upon resumption of body functions to a level above the designated parameters. Also, if desired, the vibration may be in the form of bursts spaced by very brief intervals, or a sweeping change in frequency can be provided. For example, where a fixed frequency is selected, it may fall within the range of 175–400 Hz with the preferred range being 200–300 Hz. The optimum fixed frequency is 240–260 Hz. As indicated, the stimulation may be in accordance with a preprogrammed duty cycle that provides continuous cyclical operation of an ascending sweep frequency that may vary rapidly from a low level, such as 150 Hz up to 380 Hz or more. Further, it may take the form of spaced bursts of a selected intensity. The intended purpose is to avoid infant habituation by applying a variable fixed or sweep mode.

Voltage levels may be controlled by the amplifier provided that care is exercised to avoid the generation of undesirably excessive heat at the vibrator pad. While attachment of the pad to the infant may vary in location, it is generally preferred that the pad be placed at a tactilely sensitive area, such as the bottom of the foot, the hand, etc. This tactilely sensitive area is also heat sensitive. A limited amount of heat is acceptable, yet care in controlling the voltage is necessary due to the location of the vibrator stimulus. Accordingly, suggested voltage levels typically fall within the range of 6 to 12 volts with operating levels being about 9 to 11 volts. It will be appreciated that the voltage may vary depending on the frequency employed. Additionally, the vibrator is activated for only brief periods of time so that excessive heat generation is unlikely.

The system also provides for bypassing the monitor and comparator functions by providing a manual actuator 60, such as a manually operated button placed at an appropriate location relative to the infant. The caretaker or nurse need simply press such a button to send a signal from the manual actuator 60 to the intervention decision function 40 in order to activate the vibratory stimulator 22. Alternatively, a wireless remote control 62 can be incorporated into the system to provide a similar actuation.

As shown in FIG. 3, a four channel recording chart may be used at display printout 46. It will be appreciated that other recording chart forms may readily be employed depending on the functions being monitored. In FIG. 3, each channel is labeled beneath the specific graphic display to which it relates. For example, the heart rate is recorded in the uppermost track, followed by respiration, nasal airflow and, finally, the track indicating the activation and deactivation of the vibrator. Since the tracks or channels are on the same chart, they are in synchronous alignment so that it is possible to note the simultaneous variations in chest respiration, nasal flow and vibrator actuation prior to and following the onset of an apnea episode. The onset of central apnea is perhaps best shown in this recording as a cessation of respiration that measures chest wall movement or thoracic impedance. A flattening of the nasal thermistor track and deceleration of the heart rate also are recorded. At fourteen seconds after onset, the vibrotactile stimulator is shown as having been activated and stimulated the foot of the premature neonate for five seconds. This is shown to be sufficient to cause an improvement in the respiration, nasal air flow and heart rate with subsequent return to their baseline values.

As will be apparent to persons skilled in the art, various modifications and adaptations of the system above described will become readily apparent without departure from the spirit and scope of the invention.

I claim:

1. A vibrotactile stimulator system for detecting and interrupting apnea in infants comprising (1) a multi-sensing monitor for sensing a plurality of physiological functions including means for detecting the respiratory rate of the infant and signal output means for reporting signals from said detecting means;

(2) a vibrotactile sensory stimulator including a cutaneous vibrator for engaging a peripheral sensory area on the infant, said vibrator being cyclically operable at a frequency above about 150 Hz to stimulate the infant and interrupt the apneic episode; and (3) a control interface between the multi-sensing monitor and the stimulator for comparing the reported signals from the monitor for each physiological function with a preprogrammed standard to determine variations from the standard, said interface including means for integrating the variations for different functions and assessing a combination of said variations to indicate an apneic condition in the infant and means for triggering a timing means for delaying the transmission of a stimulator actuation until the apneic condition has persisted for a selected period, said interface including intervention output means for signaling actuation of the vibrotactile stimulator.

2. The vibrotactile stimulator system of claim 1 wherein the vibrotactile stimulator includes means for selecting vibrator operating parameters, said selector means being responsive to said control interface to provide manual or automatic selection of the operating parameters.

3. The vibrotactile stimulator system of claim 1 wherein said vibrator operates at a frequency in a range up to 400 Hz.

4. The vibrotactile stimulator system of claim 3 wherein said vibrator frequency sweeps rapidly through said range.

5. The vibrotactile stimulator system of claim 1 wherein the vibrotactile stimulator includes amplifier means for amplifying the input signal to the vibrator.

6. The vibrotactile stimulator system of claim 1 wherein the vibrotactile stimulator includes means for selecting vibrator operating parameters of intensity, frequency and periodicity, and the control interface includes input selection means for selecting individualized and preprogrammed standards.

7. The vibrotactile stimulator system of claim 1 wherein the control interface includes means for selecting standards for the functions being monitored, means for recognizing the variations from the standard, and means for determining the duration of the variations from the standard to initiate activation of the intervention output means.

8. The vibrotactile stimulator system of claim 1 wherein the control interface includes input selection means for controlling the operating of the interface, said input selection means providing for the selection of individualized and preprogrammed standards, means for recognizing the variations from the standard to initiate activation of the intervention output means.

9. The vibrotactile stimulator system of claim 1 wherein the control interface includes input selection means for controlling the operating of the interface to initiate activation of the intervention output means and memory pickup means responsive to a signal from the intervention output means to actuate an event display incorporating the reporting signals from the monitor for a period prior to initiation of the intervention output.

10. The vibrotactile stimulator system of claim 1 including a manual actuator for actuating the vibrotactile stimulator.

11. The vibrotactile stimulator system of claim 10 wherein the manual actuator includes a remote control unit.

12. The vibrotactile stimulator system of claim 1 wherein the monitor includes means for selecting the detecting means being monitored and display means for displaying the reporting signals.

13. The vibrotactile stimulator system of claim 1 wherein the monitor includes means for detecting oxygen saturation.

14. The vibrotactile stimulator system of claim 1 wherein the monitor includes means for detecting nasal air flow.

15. The vibrotactile stimulator system of claim 1 wherein the monitor includes means for selecting the detecting means being monitored and displaying the reporting signals; the vibrotactile stimulator includes means for selecting vibrator operating parameters and the control interface includes input selection means for controlling the operating of the interface, said input selection means providing for the selection of individualized and preprogrammed standards.

16. The vibrotactile stimulator system of claim 1 wherein the monitor includes means for detecting oxygen saturation and display means for displaying the reporting signals; and the vibrotactile stimulator includes means for selecting vibrator operating parameters, including intensity, frequency and periodicity, and amplifier means for amplifying the input signal to the vibrator, said selector means being controlled by said control interface to provide manual or automatic selection of the operating parameters.

17. A method for the detection and vibrotactile interruption of apnea in infants comprising the steps of (1) monitoring at least the heart rate and respiratory rate functions of the infant;

(2) applying to the infant a vibrotactile sensory stimulator including a cutaneous vibrator for engaging a peripheral sensory area on the infant, said vibrator being operable at a frequency above about 150 Hz to stimulate the infant and interrupt the apneic episode;

(3) providing a control interface between the monitor and the stimulator for comparing signals from the monitor with a preprogrammed standard to determine variations from the standard, the interface including an intervention decisions mode for integrating the variations for different functions and assessing a combination of said variations to indicate an apneic condition in the infant and delaying transmission of a stimulator activation signal by actuation of a timer until the apneic condition has persisted for a selected period; and (4) actuating the cutaneous vibrator in response to the detection of an apneic condition to stimulate the infant and interrupt the apneic condition.

18. The method of claim 17 including the steps of monitoring the infant's oxygen saturation level, selecting the standards for the functions being monitored, recognizing the variations from the standard, and determining the duration of the variations from the standard to initiate activation of the vibrator.

19. The method of claim 17 wherein said vibrator operates at a frequency in a range up to 400 Hz.

20. The method of claim 17 including the step of monitoring nasal air flow.

21. The method of claim 17 including the step of displaying the monitored signals on a recording media for a period extending back to prior to onset of the apneic condition.

22. A multi-sensing system for detecting apnea in infants while obviating false apneic signals comprising (1) a multi-sensing monitor for sensing a plurality of physiological functions including means for detecting the respiratory rate of the infant and signal output means for reporting signals from said detecting means;

(2) intervention output means for signaling an apneic condition; and (3) a control interface between the multi-sensing monitor and the intervention output means for comparing the reported signals from the monitor for each physiological function with a preprogrammed standard to determine variations from the standard, said interface including means for integrating the variations for different functions and assessing a combination of said variations to indicate an apneic condition in the infant and means for triggering a timing means for delaying the transmission of an intervention actuation until the apneic period has persisted for a selected period, said interface including means for activating said intervention output means.

23. The multi-sensing system of claim 22 wherein the control interface includes means for selecting standards for the functions being monitored, means for recognizing the variations from the standard, and means for determining the duration of the variations from the standard to initiate activation of the intervention output means.

24. The multi-sensing system of claim 22 wherein the control interface includes input selection means for controlling the operating of the interface, said input selection means providing for the selection of individualized and default standards, means for recognizing the variations from the standard to initiate activation of the intervention output means.

25. The multi-sensing system of claim 22 wherein the control interface includes input selection means for controlling the operating of the interface to initiate activation of the intervention output means and memory pickup means responsive to a signal from the intervention output means to actuate an event display incorporating the reporting signals from the monitor for a period prior to initiation of the intervention output.

26. The multi-sensing system of claim 22 wherein the monitor includes means for detecting oxygen saturation.

27. The multi-sensing system of claim 22 wherein the monitor includes means for detecting nasal air flow.

28. The multi-sensing system of claim 22 wherein the intervention output means for signaling an apneic condition includes a sensory alerting signal.

* * * * *